United States Patent [19]
Tibbs

[11] 3,941,130
[45] Mar. 2, 1976

[54] SEQUENTIAL TRIGGER RELEASE FOR INJECTION DEVICE

[76] Inventor: Robert C. Tibbs, Hospital Drive, Cleveland, Miss. 38732

[22] Filed: Mar. 18, 1975

[21] Appl. No.: 559,505

[52] U.S. Cl............................ 128/218 A; 128/218 F
[51] Int. Cl.².......................................... A61M 5/22
[58] Field of Search ........ 128/218 A, 218 R, 218 F, 128/218 P, 218 PA, 215, 216, 217, 173, 224; 222/52

[56] References Cited
UNITED STATES PATENTS

| | | | |
|---|---|---|---|
| 2,531,267 | 11/1950 | Harnisch | 128/218 F |
| 2,671,448 | 3/1954 | Harnisch | 128/218 F |
| 3,605,742 | 9/1971 | Tibbs | 128/218 F |
| 3,702,608 | 11/1972 | Tibbs | 128/218 F |
| 3,712,301 | 1/1973 | Sarnoff | 128/218 A |
| 3,729,003 | 4/1973 | Hurschman | 128/218 F X |

Primary Examiner—John D. Yasko
Attorney, Agent, or Firm—Clarence A. O'Brien; Harvey B. Jacobson

[57] ABSTRACT

An injection device for a hypodermic syringe including structure for supporting a syringe and projecting the needle of the syringe into a skin tissue area against which a predetermined portion of the injection device has been placed. Also structure is provided for slightly retracting the plunger of the syringe relative to the barrel portion thereof during the projection of the needle of the syringe into the adjacent skin tissue area and further structure is provided for shifting the piston portion of the syringe, relative to the barrel portion thereof, in order to express the liquid contents of the syringe through the needle thereof after the needle has been projected in order to force the needle carried by the barrel portion of the syringe into the adjacent skin tissue. Finally, the injection device includes a pair of individual actuators for effecting projection of the syringe to displace the needle portion thereof into adjacent skin tissue and to thereafter shift the plunger portion of the syringe relative to the barrel portion thereof in order to express the liquid contents of the syringe therefrom and a single operator is operatively associated with the actuators and shiftable from an inactive position to sequential active positions in order to sequentially effect operation of the aforementioned actuators.

12 Claims, 7 Drawing Figures

U.S. Patent March 2, 1976 Sheet 1 of 2 3,941,130
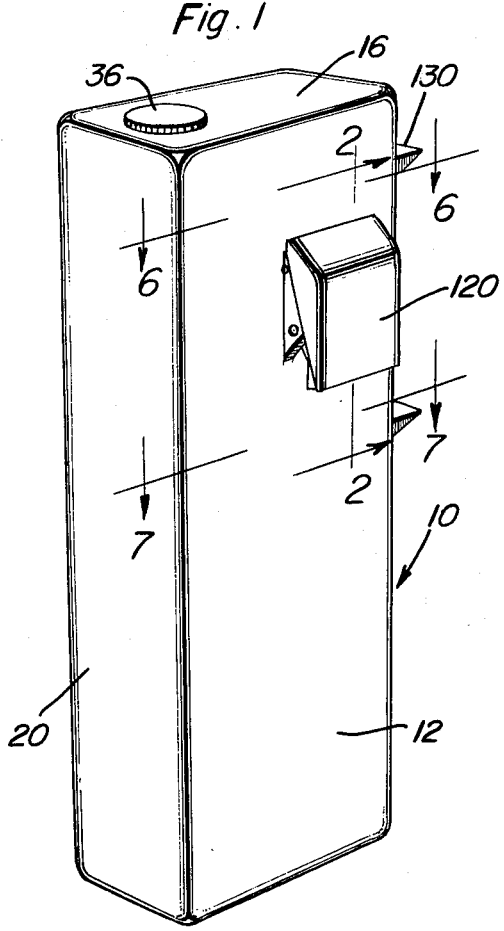
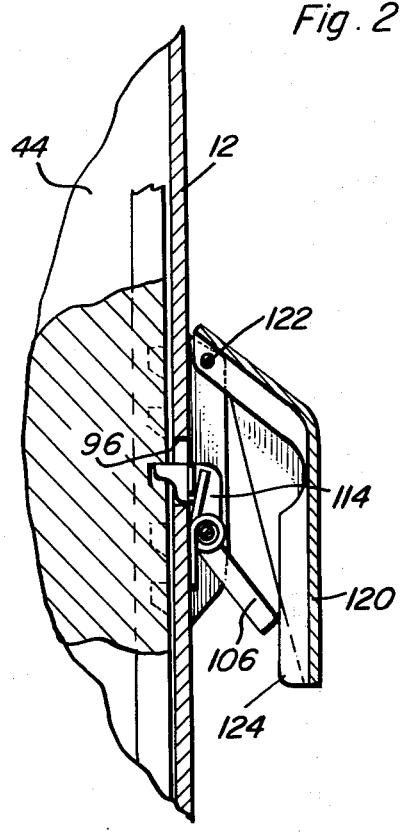
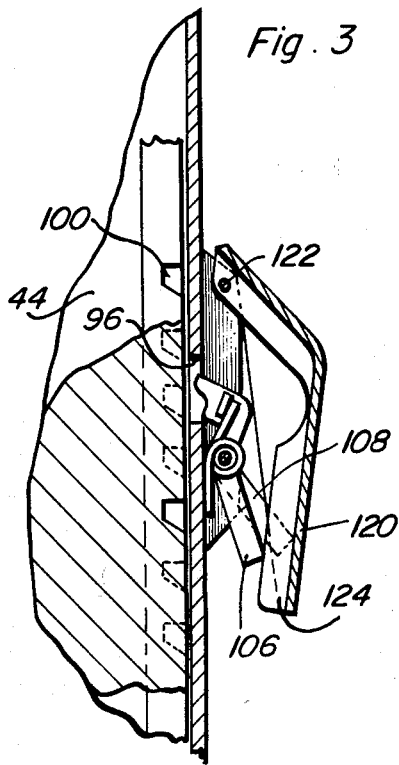
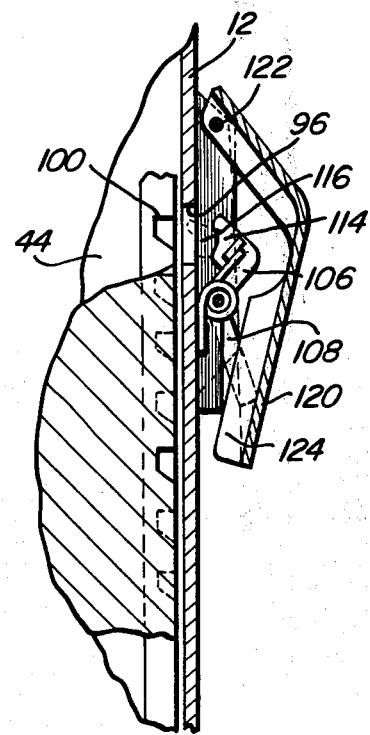

SEQUENTIAL TRIGGER RELEASE FOR INJECTION DEVICE

BACKGROUND OF THE INVENTION

This invention comprises an improvement on the injection devices disclosed in my prior U.S. Pat. Nos. 3,605,742 and 3,702,608.

Various forms of spring-equipped syringe holders and actuators have been heretofore provided. Some of these previous devices include structure by which an associated syringe may be projected in order to extend the needle portion thereof for penetration into adjacent skin tissue and additional structure whereby the plunger portion of the syringe may be advanced relative to the barrel portion thereof by spring pressure in order that the liquid contents of the syringe may be expressed from the needle portion thereof beneath the penetrated skin tissue. However, these previous devices have been at best awkward to operate in that they include variously remotely located trigger members for independently actuating the spring structure for projecting the syringe and the spring structure for subsequently advancing the plunger portion of the syringe relative to the barrel portion thereof.

Examples of previously patented devices of this type and other syringe holders including some of the basic structure of the instant invention are disclosed in U.S. Pat. Nos. 2,742,116, 2,605,766, 2,671,448, 2,752,918, 2,960,087 and 3,055,362.

BRIEF DESCRIPTION OF THE INVENTION

The injection device of the instant invention includes a support having a syringe barrel holder mounted thereon for reciprocal shifting along a predetermined path in opposite first and second directions for projecting and retracting, respectively, a needle carried by a syringe mounted on the holder. A syringe plunger holder is supported from the barrel holder for reciprocal shifting along the same path and structure is provided for yieldingly biasing the holders in the first direction in addition to first and second deactivatable structure for retaining the barrel and plunger holders, respectively, against movement in the first direction relative to the support. The first and second deactivatable structures comprise independently operable triggers and a trigger actuator is shiftably supported from the support and sequentially movable from an inactive rest position to first and second active positions for operating the first and second triggers. Accordingly, a single trigger operator is provided for sequentially operating the two triggers of the injection device.

The main object of this invention is to provide an automatic syringe holder including structure for sequentially projecting a syringe and thus the syringe needle supported therefrom and shifting the plunger portion of the syringe relative to the barrel portion thereof to express the liquid contents of the syringe barrel through the syringe needle.

Another object of this invention, in accordance with the immediately preceding object, is to provide independently operable triggers actuatable to release the syringe for projection of the needle thereof and to release the structure whereby the plunger of the syringe will be forwardly displaced relative to the barrel portion for expressing the liquid contents of the syringe through the needle thereof in addition to a single operator for the triggers which may be sequentially shifted toward two active positions from an inactive position thereof in order to operate the two trigger members in proper sequence.

Another very important object of this invention is to provide an apparatus in accordance with the preceding object and including means by which the extent of projection of the syringe and thus the syringe needle supported therefrom as well as shifting of the syringe plunger relative to the syringe barrel may be adjusted.

A final object of this invention to be specifically enumerated herein is to provide a syringe holding injection device in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the injection device of the instant invention;

FIG. 2 is a fragmentary enlarged vertical sectional view taken substantially upon the plane indicated by the section line 2—2 of FIG. 1 and illustrating the operator for the two trigger portions of the injection device in its inactive position and the two trigger portions in their operative positions;

FIG. 3 is an enlarged fragmentary vertical sectional view similar to FIG. 2 but with the operator in a first active position thereof actuating one of the triggers;

FIG. 4 is an enlarged fragmentary vertical sectional view similar to FIGS. 2 and 3 but with the operator in the second active position thereof and both of the triggers in the released positions thereof;

DETAILED DESCRIPTION OF THE INVENTION

Figure 5:
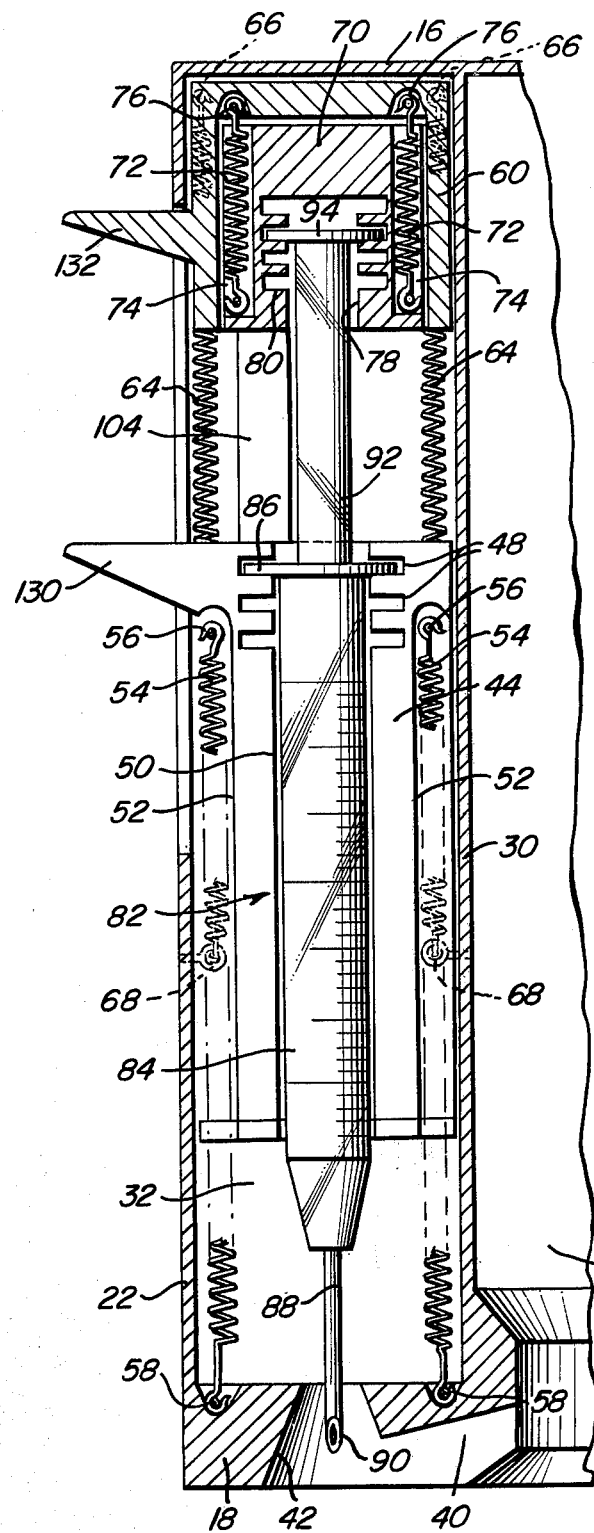
FIG. 5 is an enlarged fragmentary vertical sectional view of the injection device illustrating the hypodermic syringe supporting and syringe and syringe plunger advancing structure of the invention.
Figure 6:
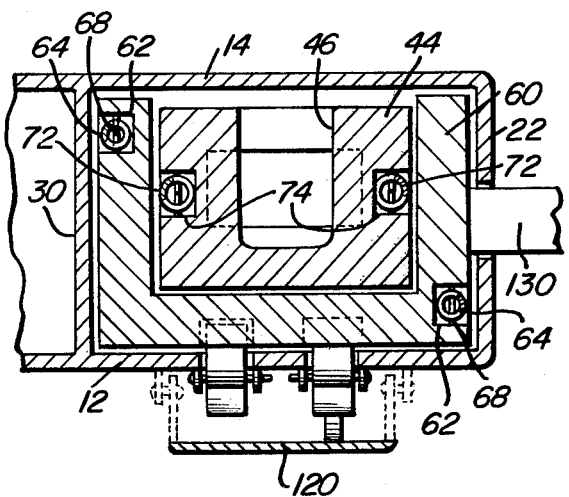
FIG. 6 is a fragmentary enlarged horizontal sectional view taken substantially upon the plane indicated by the section line 6—6 of FIG. 1.
Figure 7:
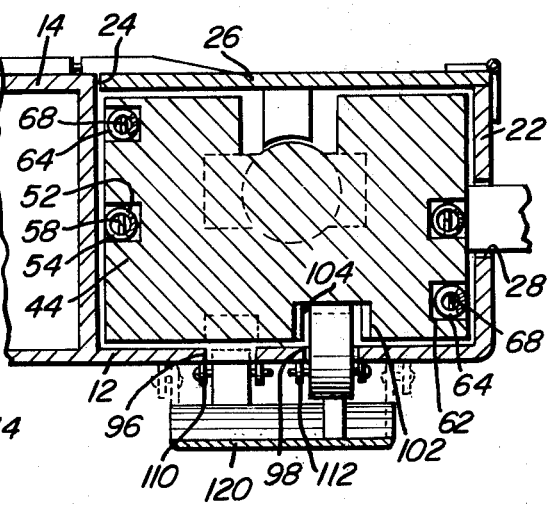
FIG. 7 is a fragmentary enlarged horizontal sectional view taken substantially upon the plane indicated by the section line 7—7 of FIG. 1.

Referring now more specifically to the drawings, the numeral 10 generally designates a vertically elongated support housing including front and rear walls 12 and 14, top and bottom walls 16 and 18 and opposite side walls 20 and 22. The rear wall 14 has an access opening 24 formed therein provided with a hinged closure 26. The side wall 22 has an upstanding slot 28 formed therein and the interior of the housing includes a front-to-rear extending partition 30 dividing the interior of the housing into first and second compartments 32 and 34. The top wall 16 has an access opening (not shown) formed therein closed by a removable plug 36 and access to the compartment or chamber 34 may be gained by removal of the plug 36.

The chamber or compartment 34 is designed to receive a pressurized container such as that disclosed in U.S. Pat. No. 3,605,742 and accompanying means (not shown) is provided for opening the outlet valve of such a container to direct a discharge of the pressurized fluid therein through the passageway or port 40 which communicates with an opening 42 formed through that portion of the bottom wall 18 defining the lower extremity of the chamber or compartment 32, whereby the discharged fluid will be directed toward the zone of skin tissue against which the bottom wall is placed in alignment with the port 40 and opening 42, see FIG. 5.

A tubular syringe barrel holder 44 is slidably mounted in the compartment or chamber 32 and includes a laterally outwardly opening slot 46. In addition, the interior of the holder 44 includes vertically spaced pairs of opposite side horizontal slots 48 which open into the central passage 50 defined through the holder 44 and also endwise through the wall of the holder 44 through which the slot 46 opens. Remote corner portions of the holder 44 are provided with upstanding grooves 52 and the upper ends of a pair of expansion springs 54 are anchored in the upper ends of the grooves 52 as at 56 while the lower ends of the expansion springs 54 are anchored to the bottom wall 18 as at 58. Thus, the expansion springs 54 serve to yieldingly bias the syringe barrel holder downwardly in the chamber 32.

A downwardly opening syringe plunger holder 60 is slidably mounted in the upper end of the chamber 32 above the holder 44 and opposite corner portions of the holder 60 include outwardly opening grooves 62 in which the upper ends of a pair of expansion springs 64 are anchored as at 66. The lower ends of the springs 64 are anchored to lower portions of the side wall 22 and partition 30 as at 68 and thus the springs 64 serve to yieldingly downwardly bias the syringe plunger holder 60.

An anchor block 70 is slidingly disposed within the syringe plunger holder 60 and a pair of expansion springs 72 have their lower ends anchored in grooves 74 formed in the block 70 and their upper ends anchored to the inner upper portions of the syringe plunger holder 60 as at 76. The anchor block 70 is provided with a slot 78 corresponding to the slot 46 and additionally includes slots 80 corresponding to the slots 48.

A syringe assembly 82 has its barrel portion 84 disposed within the slot or passage 50 and the upper finger-engaging tabs 86 of the barrel portion 84 are engaged in a corresponding pair of slots 48, a conventional hypodermic syringe needle 88 being mounted on the lower discharge end of the barrel portion 84 with the point 90 of the needle disposed within the opening 42.

The syringe assembly 82 further includes a plunger 92 including finger-engageable tabs 94 on its upper end. The upper end of the plunger 92 is received within the slot 78 and the tabs 94 are receivable in a corresponding pair of the slots 80.

With attention now invited more specifically to FIGS. 2, 3, 4 and 7 of the drawings, the front wall 12 has a pair of side-by-side access openings 96 and 98 formed therein. The syringe barrel holder 44 includes vertically extending rack gear teeth 100 formed in the side thereof opposing the inner surface of the front wall 12 and the rack gear teeth 100 are registered with the opening 96. In addition, the syringe barrel holder 44 includes a vertically extending groove 102 formed therein registered with the opening 98 and the syringe plunger holder 60 includes a depending rack gear 104 which is slidably received in the groove 102 and is registered with the opening 98. A pair of side-by-side spring-biased ratchet dogs 106 and 108 are pivotally supported from the exterior of the front wall 12 as at 110 and 112, respectively, and include detent portions 114 and 116 which are projectable through the openings 96 and 98, respectively, into engagement with the rack gear teeth 100 and the rack gear 104.

A pivoted combined cover and ratchet dog actuator 120 is swingably supported from the exterior of the front wall 12 as at 122 and overlies the ends of the ratchet dogs 106 and 108 remote from the detent portions 114 and 116 thereof. The actuator 120 includes a rib 124 which is registered with the ratchet dog 106 and it may therefore be seen from a comparison of FIGS. 3 and 4 of the drawings that when the actuator 120 is depressed the rib 124 first contacts the ratchet dot 106 so as to pivot the latter in a direction retracting the detent portion 114 from engagement with the rack gear teeth 100. Thereafter, further inward movement of the lower end of the actuator 120 causes the end of the ratchet dog 108 remote from the detent portion 116 thereof to be inwardly displaced toward the front wall 12 and thereby swings the detent portion 116 out of engagement with the rack gear 104.

The syringe barrel holder 44 includes a finger-engageable portion 130 which projects outwardly through and is slidably receivable in the slot 28 formed in the side wall 22 and the syringe plunger holder 60 includes a similar finger-engageable portion 132 which also projects outwardly through and is slidably received in the slot 28.

In operation, the syringe assembly 82 is positioned as illustrated in FIG. 5 of the drawings through the closure 26 after the holders 44 and 60 have been raised to the positions thereof illustrated in FIG. 5. Thereafter, the closure 26 is closed and the bottom wall 18 of the housing 10 may be placed against the skin area in which fluid within the barrel portion 18 is to be injected. Then, the combined cover and detent actuator 120 is inwardly depressed from the position thereof illustrated in FIG. 2 of the drawings to the position thereof illustrated in FIG. 3 whereby the ratchet dog 106 will be pivoted to a position with the detent portion 114 thereof withdrawn from the rack gear teeth 100. When this has been accomplished, the expansion springs 54 will bias the holder 44 and the barrel portion 84 downwardly in the compartment 32 to advance the point 90 of the needle 88 into the skin immediately beneath the bottom wall 18. Upon downward movement of the barrel 84 with the holder 44, a downward thrust is also applied to the plunger 92. However, downward movement of the plunger 92 is slightly resisted by the expansion of the springs 72 and thus aspiration is accomplished by a slight outward movement of the plunger 92 relative to the barrel portion 84. Thereafter, the single combined cover and detent actuator 120 is first inwardly depressed at its lower end so as to also engage the ratchet dog 108 whereby the latter is pivoted to the position thereof illustrated in FIG. 4 with the detent portion 116 thereof retracted from the rack gear 104. This of course allows the syringe plunger holder 60 to be biased downwardly under the influence of the springs 64 and the plunger 92 will be inwardly displaced relative to the barrel portion 84 so as to force the fluid material within the barrel portion 84 outwardly therefrom through the needle 88.

By utilizing a single combined cover and detent actuator such as the actuator 120 it is substantially impossible for the wrong ratchet dog to be initially depressed. Further, if only minimal air is utilized in depressing the actuator 120, the ratchet dogs 106 and 108 will be sequentially actuated in the proper manner.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In combination, a support, a syringe barrel holder mounted on said support for reciprocal shifting along a predetermined path relative to said support in opposite first and second directions for projecting and retracting, respectively, a needle carried by a syringe mounted on said holder, a syringe plunger holder supported from said barrel holder for reciprocal shifting along said path relative to said barrel holder, means yieldingly biasing said holders in said first direction, first and second deactivatable means for retaining said barrel and plunger holders, respectively, against movement in said first direction relative to said support, said first and second deactivatable means including first and second latch members, respectively, shiftably supported from said support for movement between active and inactive positions and retentively engaging said holders when in said active positions, an operator guidingly mounted on said support for back and forth movement between an inactive position, a first active position and a second active position shifted through said first active position, said latch members and said operator including coacting means operable to shift said first latch member from its active position to its inactive position upon movement of said operator from its inactive position to its first active position and to shift said second latch member to its inactive position upon subsequent movement of said operator through its first active position to its second active position.

2. The combination of claim 1 wherein said first and second latch members are pivotally supported from said support.

3. The combination of claim 2 wherein said operator is pivotally mounted from said support and includes a hand digit engageable portion accessible from the exterior of said support.

4. The combination of claim 3 wherein said operator comprises a pivoted lever whose hand digit engageable portion defines a cavity within whose boundaries said latch members are substantially entirely enclosed.

5. The combination of claim 1 including spring means connected between said support and said latch members yieldingly biasing said latch members toward their active positions.

6. The combination of claim 1 including spring means connected between said operator and said support yieldingly biasing said operator toward its inactive position.

7. The combination of claim 6 wherein said first and second latch members are pivotally supported from said support.

8. The combination of claim 7 wherein said operator is pivotally mounted from said support and includes a hand digit engageable portion accessible from the exterior of said support.

9. The combination of claim 8 wherein said operator comprises a pivoted lever whose hand digit engageable portion defines a cavity within whose boundaries said latch members are substantially entirely enclosed.

10. The combination of claim 1 wherein said second deactivatable means includes means yieldingly resisting movement of said plunger holder in said first direction as said barrel holder is moved in said first direction.

11. The combination of claim 1 wherein said barrel holder includes means for supporting said syringe barrel in adjusted shifted positions along said path relative to said barrel holder.

12. The combination of claim 1 wherein said plunger holder includes means for supporting said syringe plunger in adjusted shifted positions along said path relative to said plunger holder.

* * * * *